United States Patent [19]

Haag et al.

[11] 4,357,258
[45] Nov. 2, 1982

[54] STABLE EMULSIONS OF P-HYDROXYBENZOIC ACID ESTERS AND METHOD OF PREPARATION

[75] Inventors: Thomas E. Haag, St. Louis; Steven R. Freebersyser, Florissant; Donald F. Loncrini, Ellisville, all of Mo.

[73] Assignee: Mallinckrodt, Inc., St. Louis, Mo.

[21] Appl. No.: 199,718

[22] Filed: Oct. 23, 1980

[51] Int. Cl.$^3$ .............................................. B01J 13/00
[52] U.S. Cl. .................................... 252/312; 252/311
[58] Field of Search ................................ 252/311, 312

[56] References Cited

U.S. PATENT DOCUMENTS 3,097,131  7/1963  Ueno et al. .
4,309,564  1/1981  Loncrini et al. .

Primary Examiner—Lucille M. Phynes
Attorney, Agent, or Firm—Senniger, Powers, Leavitt & Roedel

[57] ABSTRACT

A heat and freeze-thaw stable, oil-in-water emulsion is comprised of from approximately 10% to 60% by weight of a eutectic oil containing a mixture of three or more lower alkyl esters of p-hydroxybenzoic acid, from approximately 1.5% to 5.0% by weight of an emulsifying agent which may be gelatin, casein, collagen, glyceryl oleate, the ammonium or sodium salt of sulfated nonylphenoxypoly(ethyleneoxy) ethanol or mixtures thereof, from approximately 3% to 10% by weight of sorbitol and the balance water. The method of preparing such emulsions is also disclosed.

20 Claims, No Drawings

STABLE EMULSIONS OF P-HYDROXYBENZOIC ACID ESTERS AND METHOD OF PREPARATION

BACKGROUND OF THE INVENTION

This invention relates to emulsions useful in effecting antimicrobial activity against various micro-organisms and, more particularly, to novel oil-in-water emulsions containing lower alkyl esters of p-hydroxy-benzoic acid and which are freeze-thaw and heat stable in practical use.

Heretofore, it has been known that certain p-hydroxybenzoic acid lower alkyl esters such as iso-propyl p-hydroxybenzoate, isobutyl p-hydroxybenzoate and n-butyl p-hydroxybenzoate are useful as preservatives. Ueno U.S. Pat. No. 3,097,131 discloses that eutectic mixtures of p-hydroxybenzoic acid alkyl esters may be emulsified in an aqueous solution containing such colloid protecting substances as gelatin, carboxymethyl cellulose and the like. However, it is not believed that such emulsions have the desired degree of heat stability or freeze stability for all applications and also may be subject to "breaking" or separating into two phases. Swift U.S. Pat. No. 3,085,889 discloses the use of sorbitol to impart freeze-thaw stability to asphalt emulsions, resin emulsions and rubber emulsions, but does not suggest that heat stability for emulsions can thereby be achieved. In the copending, coassigned application Ser. No. 199,719, now U.S. Pat. No. 4,309,564. of Donald F. Loncrini and John J., Taylor entitled Methods for Preparing Eutectic Mixtures of p-Hydroxybenzoic Acid Esters, incorporated herein by reference, there are described methods for preparing eutectic oil mixtures of three or more lower alkyl esters of p-hydroxybenzoic acid such as isopropyl p-hydroxybenzoate, isobutyl p-hydroxybenzoate and n-butyl p-hydroxybenzoate. It would be advantageous to provide means for formulating such eutectic oil mixtures into oil-in-water emulsions which exhibit freeze-thaw and heat stability for use as antimicrobial agents or compositions.

SUMMARY OF THE INVENTION

Among the several objects of the invention may be noted the provision of novel oil-in-water emulsions containing eutectic oil mixtures of three or more lower alkyl esters of p-hydroxybenzoic acid; the provision of such emulsions which are freeze-thaw and heat stable; and the provision of methods of preparing such emulsions. Other objects and features will be in part apparent and in part pointed out hereinafter.

Briefly, the present invention is directed to a stable, oil-in-water emulsion which comprises from approximately 10% to 60% by weight of a eutectic oil containing a mixture of three or more lower alkyl esters of p-hydroxybenzoic acid, from approximately 1.5% to 5.0% by weight of an emulsifying agent which may be gelatin, casein, collagen, glyceryl oleate, the ammonium or sodium salt of sulfated nonylphenoxypoly(ethyleneoxy) ethanol or mixtures thereof, from approximately 3% to 10% by weight of sorbitol and the balance water. The invention is also directed to the method of preparing such emulsions.

DESCRIPTION OF THE PREFERRED EMBODIMENTS

In accordance with the present invention, it has now been found that when sorbitol is incorporated in oil-in-water emulsions of eutectic oil mixtures of three or more lower alkyl esters of p-hydroxybenzoic acid and certain emulsifying agents, the resulting emulsions exhibit enhanced freeze-thaw and heat stability. By freeze-thaw stability is meant the ability of an emulsion to withstand at least four freeze-thaw cycles. By heat stability is meant the ability of an emulsion to remain as an emulsion for at least three weeks at 50° C.

The eutectic oil mixtures of three or more lower alkyl esters of p-hydroxybenzoic acid to which the present invention is applicable are those, for example, whose preparation is described in the aforementioned application of Donald F. Loncrini and John J. Taylor. These eutectic mixtures are in the form of oils and are composed of three or more lower alkyl esters (i.e., alkyl groups containing 1 to 6 carbon atoms) of p-hydroxybenzoic acid such as isopropyl p-hydroxybenzoate, isobutyl p-hydroxybenzoate and n-butyl p-hydroxybenzoate in a ratio between approximately 1:1:1 and 4:2:2, preferably between 4:2.5:2.5 and 4:3:3. It will be understood that other eutectic mixtures of three or more lower alkyl esters of p-hydroxybenzoic acid such as a mixture of isopropyl p-hydroxybenzoate, sec-butyl p-hydroxybenzoate and amyl p-hydroxybenzoate, sec-butyl p-hydroxybenzoate, isobutyl p-hydroxybenzoate and n-butyl p-hydroxybenzoate, etc., may likewise be used in the practice of the invention. As disclosed in said application, such eutectic mixtures are formed in situ preferably by first reacting p-hydroxybenzoic acid and a lower alkanol such as isopropyl alcohol in the presence of an esterificatrion catalyst such as sulfuric acid to form a first lower alkyl ester of p-hydroxybenzoic acid (e.g., isopropyl p-hydroxybenzoate), reacting the resulting mixture with two or more lower alkanols (e.g., isobutyl alcohol and n-butyl alcohol) under heat to form a mixture of three or more lower alkyl esters of p-hydroxybenzoic acid (e.g., isopropyl p-hydroxybenzoate, isobutyl p-hydroxybenzoate and n-butyl p-hydroxybenzoate), quenching the reaction when the ratio of the respective lower alkyl esters of p-hydroxybenzoic acid to each other is such that the mixture thereof is liquid at room temperature, and isolating the resulting eutectic mixture. Other methods of forming such eutectic mixtures are also disclosed in the aforementioned application. These eutectic mixtures are thus formed directly without the necessity of forming and isolating the individual esters separately and then melting or otherwise blending them together to form liquid eutectic mixtures.

The stable oil-in-water emulsions of the invention may contain from approximately 10% to 60% by weight of such a eutectic oil mixture, from approximately 1.5% to 5.0% by weight of an emulsifying agent which may be gelatin, casein, collagen, glyceryl oleate, the ammonium or sodium salt of sulfated nonylphenoxypoly(ethyleneoxy) ethanol or mixtures thereof, from approximately 3% to 10% by weight of sorbitol, with the balance being water. Higher amounts of the emulsifying agent and sorbitol may be employed but are unnecessary.

The preferred emulsifying agent is gelatin. In the practice of the invention, either Type A or B gelatin (which may be hydrolyzed or 100 bloom) or Type C such as that marketed under the trade designation "Crotein SPC" by Croda Colloids Corp. may be used. The amount of gelatin required to form a stable emulsion varies with the gelatin type (i.e., bloom strength) and the amount of the eutectic oil mixture incorporated in the emulsion. For example, 3.5% by weight hydrolyzed gelatin is used to prepare a 50% eutectic oil-in-water emulsion while only 1.5% by weight of 100 bloom gelatin is used to prepare the same emulsion.

The other useful emulsifying agents in the practice of the invention are, as stated, casein, collagen, glyceryl oleate and the ammonium or sodium salt of sulfated nonylphenoxypoly(ethyleneoxy) ethanol. The latter may be the ammonium salt of sulfated nonylphenoxypoly(ethyleneoxy) ethanol marketed under the trade designations "Alipal CO-436", "Alipal EP-110", "Alipal EP-115" or "Alipal EP-120" or the sodium salt of sulfated nonylphenoxypoly(ethyleneoxy) ethanol marketed under the trade designation "Alipal CO-433", all by GAF Corporation. The glyceryl oleate may be that marketed under the trade designation "Atmos 300" by ICI United States.

In preparing emulsions containing lesser amounts (e.g., 10%) of the eutectic oil mixture, it is preferred to use a mixture of glyceryl oleate and the ammonium or sodium salt of sulfated nonylphenoxypoly(ethyleneoxy) ethanol as the emulsifying agent, for example in proportions of 1% each by weight.

It is desirable for the novel oil-in-water emulsions of the invention to have a pH on the order of approximately 7.5 to 8.0. For this purpose, it is preferred but not essential to incorporate a pH adjusting agent which may be disodium hydrogen phosphate, sodium acetate or sodium bicarbonate in an amount of approximately 1.5% by weight. We have also found that sodium phosphate tribasic ($Na_3PO_4$) and dipotassium hydrogen phosphate ($K_2HPO_4$) can also be used as a pH adjusting agent.

The sorbitol is conveniently formulated into the emulsions of the invention through the use of a 70% aqueous solution of sorbitol.

The novel emulsions of the invention are prepared by first heating the eutectic oil mixture to a temperature of approximately 50° C. to 70° C., heating an aqueous solution of the emulsifying agent and sorbitol (and pH adjusting agent if included) to the same temperature range, then adding the heated eutectic oil mixture to the heated aqueous solution and thereafter mixing and homogenizing the resulting mixture to form the desired oil-in-water emulsion.

The oil-in-water emulsions thus formed are stable over a temperature range of −20° C. to 50° C. and are both freeze-thaw and heat stable. It is believed that the sorbitol imparts or enhances this dual stability. Thus, the emulsions of the invention have the desired properties rendering them useful in the preparation of antimicrobial compositions.

The following examples further illustrate the practice of the invention.

EXAMPLE 1

A 50% oil-in-water emulsion of a eutectic oil mixture of isopropyl p-hydroxybenzoate, isobutyl p-hydroxybenzoate and n-butyl p-hydroxybenzoate in a ratio of 4:2.25:2.26, respectively, was prepared as follows.

The eutectic oil (75 g) was placed in a 150-ml beaker and heated to 70° C. in a water bath. 75 ml of water containing 6% gelatin (Type C, marketed under the trade designation "Crotein SPC" by Croda Colloids Corp., New York, N.Y.), 3% disodium hydrogen phosphate ($Na_2HPO_4$) and 6% sorbitol derived from a 70% sorbitol solution were placed in a 150-ml beaker and heated to 70° C. The eutectic oil and water solution were mixed together by simultaneously pouring them into a 250-ml beaker on a magnetic stir plate. Mixing was continued for 15 minutes following which the mixture was homogenized in a Waring blender.

The resulting emulsion contained 50% by weight eutectic oil, 4.5% by weight gelatin, 2% by weight disodium hydrogen phosphate and 4.5% by weight sorbitol, and the balance water. This emulsion withstood four freeze-thaw cycles and a 50° C. heat stability test.

EXAMPLE 2

Example 1 was repeated except that sorbitol was omitted. The resulting emulsion broke during the first freeze-thaw cycle and at 50° C. within 24 hours.

EXAMPLE 3

Example 1 was repeated in preparing a stable oil-in-water emulsion containing 50% of the eutectic oil, 3.5% gelatin (Type C hydrolyzed), 1.5% disodium hydrogen phosphate, 3% sorbitol and the balance water.

EXAMPLE 4

Example 3 was repeated in preparing a stable emulsion containing 50% of the eutectic oil, 3.5% gelatin, 1.5% disodium hydrogen phosphate, 4% sorbitol and the balance water.

EXAMPLE 5

Example 3 was repeated in preparing a stable emulsion containing 50% of the eutectic oil, 3.0% gelatin, 1.5% disodium hydrogen phosphate, 4% sorbitol and the balance water.

EXAMPLE 6

Example 1 was repeated in preparing a stable emulsion containing 50% of the eutectic oil, 1.5% gelatin (Type A, 100 bloom), 1.5% disodium hydrogen phosphate, 6% sorbitol and the balance water.

EXAMPLE 7

Example 1 was repeated in preparing a stable emulsion containing 50% of the eutectic oil, 3% casein, 1.5% disodium hydrogen phosphate, 10% sorbitol and the balance water.

EXAMPLE 8

Example 1 was repeated in preparing a stable emulsion containing 50% of the eutectic oil, 2% of the ammonium salt of sulfonated nonylphenoxypoly(ethyleneoxy) ethanol marketed under the trade designation "Alipal CO-436" by GAF Corporation, 2% glyceryl oleate marketed under the trade designation "Atmos 300" by ICI United States, 8% sorbitol and the balance water.

EXAMPLE 9

Example 1 was repeated in preparing a white stable emulsion containing 50% by weight of a eutectic oil mixture of isopropyl p-hydroxybenzoate, sec-butyl p-hydroxybenzoate and amyl p-hydroxybenzoate in a ratio of 4:1.8:4.8, respectively, 3.5% by weight gelatin (Type C hydrolyzed), 1.5% by weight disodium hydrogen phosphate, 3% by weight sorbitol and the balance water.

EXAMPLE 10

Example 1 was repeated in preparing an off-white, stable emulsion containing 50% by weight of a eutectic oil mixture of sec-butyl p-hydroxybenzoate, isobutyl p-hydroxybenzoate and n-butyl p-hydroxybenzoate in a ratio of 2.3:4:2.83, respectively, 3.5% by weight gelatin (Type C hydrolyzed), 1.5% by weight disodium hydrogen phosphate, 2% by weight sorbitol and the balance water.

EXAMPLE 11

Example 1 was repeated in preparing a dull white, stable emulsion containing 50% by weight of the same eutectic oil employed in Example 1, 3.5% by weight of the same gelatin, 3.0% by weight sorbitol and the balance water. The emulsion had a pH of 7.7.

EXAMPLE 12

Example 11 was repeated except that 1.5% by weight of disodium hydrogen phosphate was also incorporated. The resulting white emulsion had a pH of 7.8.

EXAMPLE 13

Example 11 was repeated except that 3.0% by weight of disodium hydrogen phosphate was also incorporated. The resulting white emulsion had a pH of 8.3.

EXAMPLE 14

Example 11 was repeated except that 1.5% by weight of sodium acetate was also incorporated. The resulting cream-colored emulsion had a pH of 7.5.

EXAMPLE 15

Example 11 was repeated except that 1.5% by weight of sodium bicarbonate was also incorporated. The resulting white emulsion had a pH of 8.6.

EXAMPLE 16

Example 1 was repeated except that 60% by weight of the eutectic oil employed in Example 1 was incorporated.

EXAMPLE 17

Example 1 was repeated in preparing a white, stable emulsion containing 10% by weight of the same eutectic oil employed in Example 1, 1% by weight of "Alipal CO-436", 1% by weight of "Atmos 300", 8.5% by weight sorbitol and the balance water.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A stable, oil-in-water emulsion comprising from approximately 10% to 60% by weight of a eutectic oil containing a mixture of three or more lower alkyl esters of p-hydroxybenzoic acid, from approximately 1.5% to 5.0% by weight of an emulsifying agent selected from the group consisting of gelatin, casein, collagen, glyceryl oleate and the ammonium or sodium salt of sulfated nonylphenoxypoly(ethyleneoxy) ethanol and mixtures thereof, from approximately 3% to 10% by weight of sorbitol and the balance water.

2. A stable, oil-in-water emulsion as set forth in claim 1 additionally containing approximately 1.5% by weight of a pH adjusting agent selected from the group consisting of disodium hydrogen phosphate, sodium acetate, sodium bicarbonate, sodium phosphate tribasic and dipotassium hydrogen phosphate.

3. A stable, oil-in-water emulsion as set forth in claim 1 wherein said eutectic oil contains a mixture of isopropyl p-hydroxybenzoate, isobutyl p-hydroxybenzoate and n-butyl p-hydroxybenzoate.

4. A stable, oil-in-water emulsion as set forth in claim 1 wherein said eutectic oil contains a mixture of isopropyl p-hydroxybenzoate, sec-butyl p-hydroxybenzoate and amyl p-hydroxybenzoate.

5. A stable, oil-in-water emulsion as set forth in claim 1 wherein said eutectic oil contains a mixture of sec-butyl p-hydroxybenzoate, isobutyl p-hydroxybenzoate and n-butyl p-hydroxybenzoate.

6. A stable, oil-in-water emulsion as set forth in claim 1 wherein said emulsifying agent is gelatin.

7. A stable, oil-in-water emulsion as set forth in claim 1 wherein said emulsifying agent is a mixture of glyceryl oleate and the ammonium salt of sulfated nonylphenoxypoly(ethyleneoxy) ethanol.

8. A stable, oil-in-water emulsion as set forth in claim 1 wherein the emulsion contains from approximately 3% to 6% by weight of sorbitol.

9. A stable, oil-in-water emulsion as set forth in claim 2 wherein the emulsion contains approximately 1.5% by weight of disodium hydrogen phosphate.

10. A stable, oil-in-water emulsion as set forth in claim 1 wherein the emulsion contains approximately 50% by weight of said eutectic oil.

11. The method of preparing a stable, oil-in-water emulsion comprising from approximately 10% to 60% by weight of a eutectic oil containing a mixture of three or more lower alkyl esters of p-hydroxybenzoic acid, from approximately 1.5% to 5.0% by weight of an emulsifying agent selected from the group consisting of gelatin, casein, collagen, glyceryl oleate and the ammonium or sodium salt of sulfated nonylphenoxypoly(ethyleneoxy) ethanol and mixtures thereof, from approximately 3% to 10% by weight of sorbitol and the balance water, which method comprises the steps of heating said eutectic oil to a temperature of approximately 50° C. to 70° C., heating an aqueous solution of said emulsifying agent and sorbitol to a temperature of approximately 50° C. to 70° C., adding said heated eutectic oil to said heated aqueous solution, and thereafter mixing and homogenizing the resulting mixture to form said emulsion.

12. The method as set forth in claim 11 wherein the emulsion additionally contains approximately 1.5% by weight of a pH adjusting agent selected from the group consisting of disodium hydrogen phosphate, sodium acetate, sodium bicarbonate, sodium phosphate tribasic and dipotassium hydrogen phosphate and said pH adjusting agent is contained in said aqueous solution.

13. The method as set forth in claim 11 wherein said eutectic oil contains a mixture of isopropyl p-hydroxybenzoate, isobutyl p-hydroxybenzoate and n-butyl p-hydroxybenzoate.

14. The method as set forth in claim 11 wherein said eutectic oil contains a mixture of isopropyl p-hydroxybenzoate, sec-butyl p-hydroxybenzoate and amyl p-hydroxybenzoate.

15. The method as set forth in claim 11 wherein the eutectic oil contains a mixture of sec-butyl p-hydroxybenzoate, isobutyl p-hydroxybenzoate and n-butyl p-hydroxybenzoate.

16. The method as set forth in claim 11 wherein said emulsifying agent is gelatin.

17. The method as set forth in claim 11 wherein said emulsifying agent is a mixture of glyceryl oleate and the ammonium salt of sulfated nonylphenoxypoly(ethyleneoxy) ethanol.

18. The method as set forth in claim 11 wherein the emulsion contains from approximately 3% to 6% by weight of sorbitol.

19. The method as set forth in claim 12 wherein the emulsion contains approximately 1.5% by weight of disodium hydrogen phosphate.

20. The method as set forth in claim 11 wherein the emulsion contains approximately 50% by weight of said eutectic oil.

* * * * *